(12) United States Patent
Tanaka et al.

(10) Patent No.: US 6,353,016 B1
(45) Date of Patent: Mar. 5, 2002

(54) POTASSIUM CHANNEL ACTIVATORS

(75) Inventors: Mitsushi Tanaka, Kouga-gun; Masami Tsuda, Joyo; Ayatsugu Nakamura, Nara, all of (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 0 days.

(21) Appl. No.: 09/582,743

(22) PCT Filed: Jan. 13, 1999

(86) PCT No.: PCT/JP99/00103

§ 371 Date: Jun. 29, 2000

§ 102(e) Date: Jun. 29, 2000

(87) PCT Pub. No.: WO99/36068

PCT Pub. Date: Jul. 22, 1999

(30) Foreign Application Priority Data

Jan. 14, 1998 (JP) ............................. 10/005613
Mar. 3, 1998 (JP) ............................. 10/050888

(51) Int. Cl.⁷ .............................................. A61K 31/40
(52) U.S. Cl. .................... 514/422; 514/426; 514/427
(58) Field of Search ..................... 514/422, 426, 514/427

(56) References Cited

U.S. PATENT DOCUMENTS 5,998,459 A * 12/1999 Tsuda et al. ................. 514/408
6,172,102 B1 * 1/2001 Tsuda et al. ................. 514/422

FOREIGN PATENT DOCUMENTS

JP 05-246980 * 9/1993
WO WO 97/16442 * 5/1997
WO WO 98/02430 * 1/1998

* cited by examiner

Primary Examiner—Fiona T. Powers
(74) Attorney, Agent, or Firm—Eugene C. Rzucidlo; Greenberg Traurig, LLP

(57) ABSTRACT

The invention is directed to a pharmaceutical composition comprising a pyrrole derivative of the following formula [1] or its pharmaceutically acceptable salt as an active ingredient.

[1]

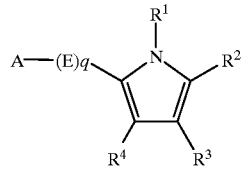

(wherein $R^1$ represents hydrogen or alkoxycarbonylamino; $R^2$ represents alkyl, aryl which may be substituted, a aromatic heterocyclyl which may be substituted, unsubstituted amino, monoalkyl-substituted amino, dialkyl-substituted amino, or cyclic amino which may be substituted; $R^3$ represents cyano or carbamoyl; $R^4$ represents hydrogen or alkyl; E represents alkylene; q represents 0 or 1; A represents methyl, aryl which may be substituted, or a aromatic heterocyclyl which may be substituted).

This pharmaceutical composition is useful as a potassium channel activator.

12 Claims, No Drawings

POTASSIUM CHANNEL ACTIVATORS

This application is a 371 of PCTJP99/00103 filed Jan. 13, 1999.

TECHNICAL FIELD

The present invention relates to a potassium channel ($K^+$-channel) activator comprising a pyrrole derivative or its pharmaceutically acceptable salt as an active ingredient. A potassium channel activator is useful for the prophylaxis or therapy of $K^+$-channel-associated physiologic disorders.

BACKGROUND ART

The potassium channel exists in a variety of cells such as nerve cells and smooth muscle cells and is involved in various physiological processes and control the homeostasis of normal cell ions. Generally potassium ions regulate the resting membrane potential of cells, and an efflux of potassium ions following depolarization of the cell membrane results in repolarization of the membrane. The potassium channel activator causes hyperpolarization of cells. Thereby, in nerve cells, suppress cellular activity to reduce the transmitters release from the nerve endings and, in smooth muscle cells, suppress the contractility.

Therefore, a potassium channel activator is considered to be of value in the therapy of nervous system disorders inducing spasmodic or ischemic responses through its action on nerve cells. Furthermore, through its action on smooth muscle cells, a potassium channel activator is expected to be useful in the therapy of various diseases such as hypertension, angina pectoris, asthma and irritable bowel syndrome.

Already known as compounds having potassium channel activating activity are benzopyran derivatives (Japanese Laid-Open S58-67683, Japanese Laid-Open H6-25233, WO 94/13297, etc.), thienopyran derivatives (WO 94/13297 etc.), benzoxazine derivatives (Japanese Laid-Open H5-70464, WO 94/13297, etc.), benzoxepine derivatives (WO 94/13297 etc.), quinoline derivatives (WO 94/13297 etc.), indole derivatives (WO 94/13297 etc.), benzocycloheptane derivatives (WO 94/13297 etc.) and pyridine derivatives (The Merck Index, 11th edition, 7407), among others.

The compound according to the present invention (hereinafter referred to as the compound of the invention) is a pyrrole derivative which is structurally different from any of the above-mentioned compounds having potassium channel activating activity. It has not heretofore been known that a pyrrole derivative ever has potassium channel activating activity.

DISCLOSURE OF INVENTION

The object of the present invention is to provide a novel potassium channel activator.

Exploring into various compounds with enthusiasm, the inventors of the present invention found surprisingly that a pyrrole derivative of the following general formula [1] has potassium channel activating activity and have completed this invention.

The present invention, therefore, is directed to a potassium channel activator composition comprising a pyrrole derivative of the following general formula [1] or a pharmaceutically acceptable salt thereof as an active ingredient.

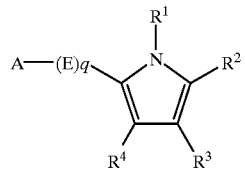

[1]

wherein $R^1$ represents hydrogen or alkoxycarbonylamino;
$R^2$ represents (i) alkyl, (ii) aryl which may be substituted, (iii) aromatic heterocyclyl which may be substituted, (iv) a group of the following formula [2]

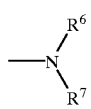

[2]

[wherein $R^6$ and $R^7$ may be the same or different and each represents (1) hydrogen or (2) alkyl (said alkyl may be substituted by (1) aryl which may be substituted by alkoxy, (2) aromatic heterocyclyl, or (3) hydroxy)], or (v) a group of the following formula [3]

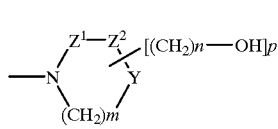

[3]

$Z^1$ and $Z^2$ may be the same or different and each represents $-CH_2-$ or $>C=O$; provided that $Z^1$ and $Z^2$ do not concurrently represent $>C=O$;
Y represents $-CH_2-$, $-O-$, $-S-$, or $>NR^9$;
$R^9$ represents hydrogen, alkyl, acyl, aryl, or aromatic heterocyclyl;
m represents an integer of 1–3; n represents an integer of 0–2; p represents 0 or 1;
in case $R^2$ represents aryl which is substituted or aromatic heterocyclyl which is substituted, the particular aryl or aromatic heterocyclyl may be substituted by 1–3 same or different members selected from the group consisting of (1) halogen, (2) alkyl which may be substituted by halogen, (3) cyano, (4) nitro, (5) alkoxycarbonyl, (6) hydroxy, (7) alkoxy (said alkoxy may be substituted by (1) halogen, (2) aryl which may be substituted by alkoxy, or (3) alkoxy), (8) $-NHSO_2R^{82}$, and (9) $-NR^{83}R^{84}$; or two adjacent substituent groups may jointly represent $-O-(CH_2)_t-O-$ (t represents 1 or 2);
$R^{82}$ represents (1) alkyl or (2) aryl which may be substituted by alkyl;
$R^{83}$ and $R^{84}$ may be the same or different and each represents (1) hydrogen, (2) alkyl, or (3) acyl; or $R^{83}$ and $R^{84}$ jointly and taken together with the adjacent N atom represent 5- through 7-membered cyclic amino;
$R^3$ represents cyano or carbamoyl;
$R^4$ represents hydrogen or alkyl;
E represents alkylene; q represents 0 or 1;
A represents (1) methyl, (2) aryl which may be substituted, or (3) aromatic heterocyclyl which may be substituted;

in case A represents aryl which is substituted or aromatic heterocyclyl which is substituted, the particular aryl or aromatic heterocyclyl may be substituted by 1–3 same or different members selected from the group consisting of (1) halogen, (2) alkyl which may be substituted by halogen, (3) cyano, (4) nitro, (5) alkoxycarbonyl, (6) hydroxy, (7) alkoxy (said alkoxy may be substituted by (1) halogen, (2) aryl which may be substituted by alkoxy, or (3) alkoxy), (8) —NHSO$_2$R$^{92}$, and (9) —NR$^{93}$R$^{94}$; or two adjacent substituent groups may jointly represent —O—(CH$_2$)$_u$—O— (u represents 1 or 2);

R$^{92}$ represents (1) alkyl or (2) aryl which may be substituted by alkyl;

R$^{93}$ and R$^{94}$ may be the same or different and each represents (1) hydrogen, (2) alkyl, or (3) acyl; or R$^{93}$ and R$^{94}$ jointly and taken together with the adjacent N atom represent 5- through 7-membered cyclic amino;

A—(E)q, R$^4$, and the double bond of the pyrrole ring may jointly, i.e.

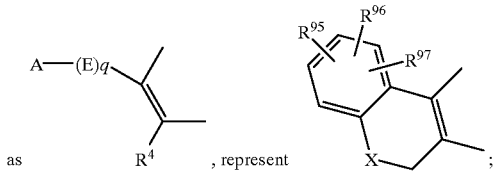

as R$^4$, represent

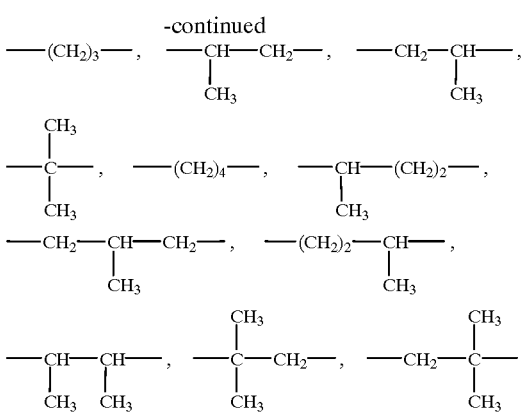

X represents —O—, —S—, or >NR$^{90}$ where R$^{90}$ represents alkyl;

R$^{95}$, R$^{96}$ and R$^{97}$ may be the same or different and each is selected from the group consisting of (1) hydrogen, (2) halogen, (3) alkyl which may be substituted by halogen, (4) cyano, (5) nitro, (6) alkoxycarbonyl, (7) hydroxy, (8) alkoxy (said alkoxy may be substituted by halogen or alkoxy), (9) —NHSO$_2$R$^{92}$ (R$^{92}$ is as defined above), and (10) —NR$^{93}$R$^{94}$ (R$^{93}$ and R$^{94}$ are as defined above); any two adjacent substituent groups among R$^{95}$, R$^{96}$, and R$^{97}$ may jointly represent —O—(CH$_2$)$_u$—O— (u is as defined above).

In the context of the present invention, the "alkyl" includes straight-chain or branched-chain alkyl groups containing 1–4 carbon atoms, such as methyl, ethyl, n-propyl, isopropyl, n-butyl, isobutyl, sec-butyl and tert-butyl.

The "aryl" includes aryl groups of 6–12 carbon atoms, such as phenyl, 1-naphthyl, 2-naphthyl, 3-biphenyl and 4-biphenyl.

The "aromatic heterocyclyl" includes groups of aromatic 5- or 6-membered rings containing 1–4 nitrogen, oxygen or sulfur atoms as ring members and the corresponding benzene-fused ring systems (however, 2-pyrrolyl and 3-pyrrolyl are excluded), thus including 2-pyridyl, 3-pyridyl, 4-pyridyl, 2-pyrimidinyl, 4-pyrimidinyl, 1-indolyl, 2-indolyl, 3-indolyl, 1-tetrazolyl, 2-furyl, 3-furyl, 2-benzofuranyl, 3-benzofuranyl, 2-thienyl, and 3-thienyl, among others.

The "alkylene" includes straight-chain or branched groups of 1–4 carbon atoms, such as the following.

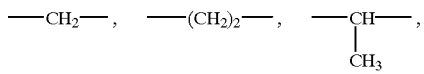

The alkyl moiety of said "alkoxy", "alkoxycarbonyl" or "alkoxycarbonylamino" includes the alkyl groups mentioned above.

The "halogen" includes fluoro, chloro, bromo and iodo.

The "acyl" includes groups of 1–7 carbon atoms, such as formyl, acetyl, propionyl, butyryl, isobutyryl, valeryl, isovaleryl, pivaloyl, hexanoyl, isohexanoyl and benzoyl.

The 5–7-membered cyclic amino represented by NR$^{83}$R$^{84}$ or NR$^{93}$R$^{94}$ includes but is not limited to 1-pyrrolidinyl, 1-piperidinyl and 1-hexamethyleneimino.

The preferred species of the compound [1] of the invention includes the compound in which R$^1$ is hydrogen, R$^2$ is NH$_2$, pyrrolidino or methyl, R$^3$ is cyano, R$^4$ is hydrogen or methyl, q is 0, and A is aryl which may be substituted or a aromatic heterocyclyl which may be substituted.

Particularly preferred examples of the compound [1] of the invention includes the following compounds.

(1) 2-Amino-3-cyano-5-(2-fluorophenyl)-4-methylpyrrole (hereinafter referred to as compound 1)

(2) 2-Amino-3-cyano-4-methyl-5-phenylpyrrole (hereinafter referred to as compound 2)

(3) 2-Amino-5-(3-chlorophenyl)-3-cyano-4-methylpyrrole (hereinafter referred to as compound 3)

(4) 2-Amino-3-cyano-5-(2-furyl)-4-methylpyrrole (hereinafter referred to as compound 4)

(5) 2-Amino-3-cyano-5-(3,4-methylenedioxyphenyl)pyrrole (hereinafter referred to as compound 5)

(6) 2-Amino-3-cyano-5-(2,4-difluorophenyl)pyrrole (hereinafter referred to as compound 6)

(7) 5-(3-Chlorophenyl)-3-cyano-2-methylpyrrole (hereinafter referred to as compound 7)

(8) 2-Amino-3-cyano-4-methyl-5-(3-nitrophenyl)pyrrole (hereinafter referred to as compound 8)

(9) 3-Cyano-2,4-dimethyl-5-phenylpyrrole (hereinafter referred to as compound 9)

(10) 3-Cyano-5-(3-ethoxyphenyl)-2-pyrrolidinopyrrole (hereinafter referred to as compound 10)

(11) 3-Cyano-5-(3,4-methylenedioxyphenyl)-2-pyrrolidinopyrrole (hereinafter referred to as compound 11)

The compound of the invention, represented by general formula [1] above, can be produced by any of the processes described in WO 96/40634.

Among species of the compound of the invention, any compound that is basic can be administered for medication in the free base form but optionally may be converted to a pharmaceutically acceptable salt by the known procedure and administered. The salt includes salts with inorganic acids such as hydrochloric acid, hydrobromic acid, sulfuric acid, phosphoric acid, and salts with organic acids such as acetic acid, citric acid, tartaric acid, maleic acid, succinic acid, fumaric acid, p-toluenesulfonic acid, benzenesulfonic acid, methanesulfonic acid.

The compound of the invention has potent activating activity on potassium channel and yet is only slightly toxic as shown in the experimental examples which appear hereinafter, so that it is useful as a prophylactic or therapeutic drug for cardiovascular diseases such as hypertension, ischemic diseases (such as angina pectoris and myocardial infarction), arteriosclerosis, hyperlipemia, congestive heart failure, arrhythmia and peripheral vascular disorders.

In addition, the compound of the invention is useful as a therapeutic drug for various disorders associated with smooth muscle contraction, such as cerebrovascular disorders (e.g. cerebrovascular spasm), peripheral vascular disorders (e.g. trichogenetic insufficiency, psilosis, coldness of limbs, etc.), respiratory disorders (reversible airway obstruction, hypersensitivity airway obstruction, asthma), gastrointestinal disorders (ulcer, irritable bowel syndrome, bile duct obliteration, etc.), visuoauditory disorders (e.g. glaucoma, ocular hypertension, etc.), urinary system disorders (renal failure, disorders accompanied with the passage of renal calculi, etc.), and genital organ disorders (erectile dysfunction, premature labor, etc.).

Furthermore, the compound of the invention is useful as a therapeutic drug for blood sugar abnormalities (hypoglycemia etc.) and as a prophylactic or therapeutic drug for disorders due to abstinence in cases of abuse of such substances as cocaine, nicotine, alcohol, and benzodiazepine, disorders which may be prevented or cured with an anticonvulsant, such as epilepsy, neuropathies arising from cerebrovascular disorders, and various nervous system disorders such as schizophrenia.

For use of the compound of the invention as a medicine, the compound can be administered, either as it is or in the form of a pharmaceutical composition containing it in a concentration of, for example, 0.1–99.5%, preferably 0.5–90%, in a pharmaceutically acceptable, nontoxic and inert carrier, to mammals inclusive of humans.

As the carrier, at least one member selected from solid, semisolid or liquid diluents, fillers and other auxiliary formulating agents is employed. The pharmaceutical composition is preferably administered in a unit dose form. The pharmaceutical composition of the present invention can be administered intravenously, orally, into the target tissue, locally (e.g. transdermally) or rectally. Dosage forms suited to the respective routes of administration should of course be selected. Particularly preferred is oral administration.

Oral administration can be made using a solid or liquid dose unit, such as neat powders, powders, tablets, sugar-coated tablets, capsules, granules, suspensions, solutions, syrups, drops, sublingual tablets and so on.

Neat powders can be prepared by comminuting the active substance to a suitable particle size. Powders can be produced by comminuting the active substance to a suitable particle size and blending the resulting particles with a similarly comminuted pharmaceutical carrier, such as fine particles of, for example, an edible carbohydrate such as starch or mannitol. Where necessary, flavoring agents, preservatives, dispersants, coloring agents, perfumes, etc. can also be added and mixed.

Capsules can be produced by filling capsule shells, such as gelatin capsule shells, with such comminuted neat powders or powders or granules prepared therefrom as described below for the manufacture of tablets. Prior to filling, a lubricant or fluidizing agent, such as colloidal silica, talc, magnesium stearate, calcium stearate, solid polyethylene glycol, etc., can be added to the powdery material. Furthermore, the bioavailability of the medicament after intake of the capsule can be improved by adding a disintegrator or solubilizer, such as carboxymethylcellulose, carboxymethylcellulose calcium, low-substitution-degree hydroxypropylcellulose, croscarmellose sodium, carboxymethylstarch sodium, calcium carbonate, sodium carbonate and so on.

The finely divided powder mentioned above may be dispersed in a vegetable oil, polyethylene glycol, glycerin or a surfactant and the resulting suspension be wrapped in gelatin sheets to provide soft capsules. Tablets can be produced by preparing a powdery mixture using an excipient, granulating or slugging it, adding a disintegrator or a lubricant, and compressing the mixture. The powdery mixture can be prepared by mixing a suitably comminuted powder of the active substance with said diluent or base and, where necessary, adding a binder (e.g. carboxymethylcellulose sodium, methylcellulose, hydroxypropylmethylcellulose, gelatin, polyvinylpyrrolidone, polyvinyl alcohol, etc.), a dissolution retardant (e.g. paraffin), a reabsorption agent (e.g. a quaternary salt) and an adsorbent (e.g. bentonite, kaolin, dicalcium phosphate). The powdery mixture may be processed into granules by wetting it with a binder, such as a syrup, starch paste, gum arabic, a cellulose solution or a polymer solution, in the first place, stirring the mixture, drying it, and pulverizing it. Instead of granulating the powder, it may be compressed with a tablet machine in the first place and crushing the crude-form slugs into granules.

The granules thus obtained can be protected against interadhesion by adding a lubricant such as stearic acid, a stearate, talc, mineral oil or the like. The lubricated mixture is then compressed. Bare tablets thus obtained can be film-coated or sugar coated.

The drug may be admixed with a free-flowing inert carrier and directly compressed into tablets without said granulation or slugging operation. A transparent or translucent protective film comprising a hermetic shellac coat, a sugar or polymer covering film, or a polished wax top coat may also utilized.

Other oral dosage forms, such as a solution, a syrup and an elixir, can also be provided as a unit dose form containing a predetermined amount of the drug in a given quantity. Syrups can be produced by dissolving the compound in suitable flavored aqueous solutions, while elixirs can be produced by using nontoxic alcoholic vehicles. Suspensions can be formulated by dispersing the compound in nontoxic vehicles. Where necessary, solubilizers and emulsifiers (e.g. ethoxylated isostearyl alcohol, polyoxyethylene sorbitol ester), preservatives and flavoring agents (e.g. peppermint oil, saccharin), among others, may also be added.

If necessary, unit dose formulations for oral administration may be microencapsulated. Such formulations may be coated or embedded in a high polymer or a wax for prolonging the duration of action or insuring a sustained release.

Administration into the target tissue can be made using a liquid unit dosage form suited for subcutaneous, intramuscular or intravenous administration, for example a solution or a suspension. Such dosage forms can be produced by suspending or dissolving a predetermined amount of the compound in an injectable nontoxic liquid vehicle such as an aqueous medium or an oily medium and, then, sterilizing the suspension or solution. For isotonizing such parenteral products, nontoxic salts or salt solutions may be added. A stabilizer, a preservative and/or an emulsifier may also be incorporated.

Rectal administration can be made using suppositories manufactured by dissolving or suspending the compound in a low-boiling water-soluble or insoluble solid, such as polyethylene glycol, cacao butter, a semisynthetic oil (e.g. Witepsol™), a higher ester (e.g. myristyl palmitate) or a mixture thereof.

The dosage as a potassium channel activator is preferably established with reference to the nature and severity of disease, patient factors such as age and body weight, the route of administration, etc. but the usual daily dose is 0.1–1000 mg/adult patient, preferably 1–500 mg/adult patient, in terms of the compound of the invention.

Dosage reduction may be warranted in some cases, while dosage escalation may be needed in others. Moreover, the above dosage may be administered in 2–3 divided doses a day.

BEST MODE FOR CARRYING OUT THE INVENTION

The following experimental examples and formulation example illustrate the present invention in further detail without defining the scope of the invention.

EXPERIMENTAL EXAMPLE 1

Effect on KCl-induced contraction of the isolated rat aorta specimen

It has been generally demonstrated that the relaxing effect of a potassium channel activator on a KCl-induced contraction in isolated preparations attenuates as the concentration of KCl is increased (Br. J. Pharmacol., 88, 103–111 (1986)). In the present experiment, potassium channel activating activity was evaluated by comparing the $pIC_{50}$ values representing the relaxing effects of the test drug on the 20 mM KCl-induced contraction and 100 mM KCl-contraction. According to Br. J. Pharmacol., 88, 103–111 (1986) referred to above, potassium channel activators produce greater relaxing effects on 20 mM KCl-induced contraction than on 100 mM KCl-induced contraction.

Male 7–13-week-old SD rats (body weights 240–480 g) were used in groups of 4–6. After the animal was bled to death under ether anesthesia, the throacic aorta was isolated and dissected into a spiral specimen about 2 mm wide×about 20 mm long. Each specimen was suspended in a 10 ml Magnus bath containing Krebs-Henseleit solution (KH solution) aerated with 95% $O_2$+5% $CO_2$ at 37° C. A tension load of 1 g was applied and with the KH solution exchanged every 20 minutes, the specimen was equilibrated for about 90 minutes. Then, the experiment was commenced. The change in tension of the specimen was recorded on a recticorder through an isometric tension transducer. The specimen was caused to contract by replacing the KH solution in the Magnus bath with 20 mM or 100 mM KCl-containing KH solution (NaCl in KH solution was replaced with an equimolar amount of KCl) and when the contractile response had reached plateau, the test drug was cumulatively applied to evaluate the relaxing effect.

The results are shown in Table 1. Each result was expressed in the average of the relaxation ratio obtained in the presence of the test drug, with the maximum relaxation found with papaverine (100 μM) being taken as the 100% relaxation response of the specimen.

TABLE 1

Effect on the KCl-induced contraction of the isolated rat aorta specimen

| | | Relaxation effect (%) | | |
|---|---|---|---|---|
| Compound No. | Concentration (μM) | 20 mM KCl-induced contraction | 100 mM KCl-induced contraction | n |
| Compound 1 | 10 | 82 | 28 | 4 |
| Compound 2 | 10 | 78 | 17 | 4–6 |
| Compound 3 | 1 | 45 | 6 | 4 |
| Compound 4 | 10 | 64 | 12 | 4–5 |
| Compound 5 | 10 | 73 | 18 | 4 |
| Compound 6 | 10 | 92 | 24 | 4 |

In the isolated rat aorta specimen, the compound of the invention showed a greater relaxing effect on 20 mM KCl-induced contraction than on 100 mM KCl-induced contraction. It is, therefore, clear that the compound of the invention has potent activaing activity on potassium channel.

EXPERIMANTAL EXAMPLE 2

Effect on the KCl-induced contraction of the isolated guinea-pig trachea specimen As in Experimental Example 1, potassium channel activating activity was evaluated by comparing the relaxing effects of the test drug on 20 mM KCl-induced contraction and 100 mM KCl-induced contraction.

Male 5–13-week-old Hartley guinea pigs (body weights 400–730 g) were used in groups of 2–4. After the animal was bled to death under ether anesthesia, the trachea was isolated and 4 tracheal strips were connected to prepare a specimen in accordance with the method of Takagi et al. (Chem. Pharm. Bull., 6, 716–720 (1958)). The experiment was performed in the same manner as described in Experimental Example 1.

The results are shown in Table 2.

TABLE 2

Effect on the KCl-induced contraction of the isolated guinea-pig trachea specimen

| | | Relaxation effect (%) | | |
|---|---|---|---|---|
| Compound No. | Concentration (μM) | 20 mM KCl-induced contraction | 100 mM KCl-induced contraction | n |
| Compound 5 | 10 | 58 | −7 | 4 |
| Compound 7 | 3 | 64 | 31 | 4 |
| Compound 8 | 3 | 58 | −2 | 2 |
| Compound 9 | 10 | 79 | 39 | 2–4 |
| Compound 10 | 3 | 37 | −15 | 4 |
| Compound 11 | 10 | 37 | 4 | 4 |

In the isolated guinea-pig trachea, the compound of the invention showed a greater relaxing effect on 20 mM KCl-induced contraction than on 100 mM KCl-induced contraction. It is, therefore, clear that the compound of the invention has potent activating activity on potassium channel.

EXPERIMANTAL EXAMPLE 3

Effect on blood pressure in anesthetized rats

Female 10–13-week-old SD rats (body weights 180–300 g) fasted from the previous day were used in groups of 2–4. The animal was placed in supine position under urethane anesthesia and the femoral artery was cannulated for blood pressure measurement. The blood pressure was recorded on a recorder through the cannula and a pressure transducer. When the blood pressure had stabilized, the test drug was administered intraduodenally and the effect on blood pressure was monitored up to 3 hours after administration.

The results are shown in Table 3. Each value is expressed as the average of % changes at the time of maximal action.

TABLE 3

Effect on blood pressure in anesthetized rats

| Compound No. | Dosage (mg/kg) | Hypotensive effect (%) | n |
|---|---|---|---|
| Compound 2 | 100 | 25.9 | 4 |
| Compound 3 | 100 | 14.1 | 4 |
| Compound 4 | 100 | 25.6 | 2 |

When administered intraduodenally, the compound of the invention showed blood pressure-lowering effects apparently ascribable to its potassium channel activating activity.

EXPERIMANTAL EXAMPLE 4

Acute toxicity test

Male 6–7-week-old ddY mice (body weights 20–40 g) were used in groups of 4. The animal was fasted from the previous day (for 16–18 hours), and using a gastric tube, the test drug in a dose of 1000 mg/kg was administered orally. The mortality of the animals were then monitored for 2 weeks. As test drugs, compound 1, compound 2 and compound 4 were respectively administered. As a result, no death was encountered in any of the compound groups.

FORMULATION EXAMPLE 1

Tablets (oral tablets)
Recipe, in 200 mg per tablet

| | |
|---|---|
| Compound 1 | 20 mg |
| Corn starch | 88 mg |
| Crystalline cellulose | 80 mg |
| Carboxymethylcellulose Ca | 10 mg |
| Light silicic anhydride | 1 mg |
| Magnesium stearate | 1 mg |

INDUSTRIAL APPLICABILITY

As set forth above, the compound of the invention is a compound having potent potassium channel activating activity and of low toxic potential and, therefore, a pharmaceutical composition comprising the compound of the invention as an active ingredient is useful as a potassium channel activator in mammals including humans.

What is claimed is:
1. A method of treating potassium-channel-associated physiologic disorder in a subject comprising administering to the subject an effective amount of a pyrrole derivative of the following formula [1] or a pharmaceutically acceptable salt thereof;

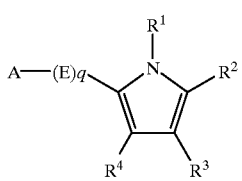

[1]

wherein $R^1$ represents hydrogen or alkoxycarbonylamino;
$R^2$ represents (i) alkyl, (ii) aryl which may be substituted, (iii) aromatic heterocyclyl which may be substituted, (iv) a group of the following formula [2]

[2]

wherein $R^6$ and $R^7$ may be the same or different and each represents (1) hydrogen or (2) alkyl (said alkyl may be substituted by (1) aryl which may be substituted by alkoxy, or (2) aromatic heterocyclyl, or (3) hydroxy), or (v) a group of the following formula [3]

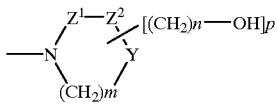

[3]

$Z^1$ and $Z^2$ may be the same or different and each represents —$CH_2$— or >C=O; provided that $Z^1$ and $Z^2$ do not concurrently represent >C=O;
Y represents —$CH_2$—, —O—, —S—, or >$NR^9$;
  $R^9$ represents hydrogen, alkyl, acyl, aryl, or aromatic heterocyclyl;
  m represents an integer of 1–3; n represents an integer of 0–2; p represents 0 or 1;
in case $R^2$ represents aryl which is substituted or aromatic heterocyclyl which is substituted, the particular aryl or aromatic heterocyclyl may be substituted by 1–3 same or different members selected from the group consisting of (1) halogen, (2) alkyl which may be substituted by halogen, (3) cyano, (4) nitro, (5) alkoxycarbonyl, (6) hydroxy, (7) alkoxy (said alkoxy may be substituted by (1) halogen, (2) aryl which may be substituted by alkoxy, or (3) alkoxy), (8) —$NHSO_2R^{82}$, and (9) —$NR^{83}R^{84}$; or two adjacent substituent groups may jointly represent —O—$(CH_2)_t$—O— (t represents 1 or 2);
$R^{82}$ represents (1) alkyl or (2) aryl which may be substituted by alkyl;
$R^{83}$ and $R^{84}$ may be the same or different and each represents (1) hydrogen, (2) alkyl, or (3) acyl; or $R^{83}$ and $R^{84}$ jointly and taken together with the adjacent N atom represent 5- through 7-membered cyclic amino;
$R^3$ represents cyano or carbamoyl;
$R^4$ represents hydrogen or alkyl;
E represents alkylene; q represents 0 or 1;
A represents (1) methyl, (2) aryl which may be substituted, or (3) aromatic heterocyclyl which may be substituted;
in case A represents aryl which is substituted or aromatic heterocyclyl which is substituted, the particular aryl or aromatic heterocyclyl may be substituted by 1–3 same or different members selected from the group consisting of (1) halogen, (2) alkyl which may be substituted by halogen, (3) cyano, (4) nitro, (5) alkoxycarbonyl, (6) hydroxy, (7) alkoxy (said alkoxy may be substituted by (1) halogen, (2) aryl which may be substituted by alkoxy, or (3) alkoxy), (8) —NHSO$_2$R$^{92}$, and (9) —NR$^{93}$R$^{94}$; or two adjacent substituent groups may jointly represent —O—(CH$_2$)$_u$—O— (u represents 1 or 2);

R$^{92}$ represents (1) alkyl or (2) aryl which may be substituted by alkyl;

R$^{93}$ and R$^{94}$ may be the same or different and each represents (1) hydrogen, (2) alkyl, or (3) acyl; or R$^{93}$ and R$^{94}$ jointly and taken together with the adjacent N atom represent 5 through 7-membered cyclic amino;

A—(E)q, R$^4$, and the double bond of the pyrrole ring may jointly, i.e.

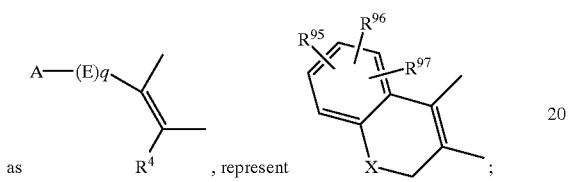

X represents —O—, —S—, or >NR$^{90}$ where R$^{90}$ represents alkyl; and

R$^{95}$, R$^{96}$ and R$^{97}$ may be the same or different and each is selected from the group consisting of (1) hydrogen, (2) halogen, (3) alkyl which may be substituted by halogen, (4) cyano, (5) nitro, (6) alkoxycarbonyl, (7) hydroxy, (8) alkoxy (said alkoxy may be substituted by halogen or alkoxy), (9) —NHSO$_2$R$^{92}$ (R$^{92}$ is as defined above), and (10) —NR$^{93}$R$^{94}$ (R$^{93}$ and R$^{94}$ are as defined above); any two adjacent substituent groups among R$^{95}$, R$^{96}$, and R$^{97}$ may jointly represent —O—(CH$_2$)$_u$—O— (u is as defined above).

2. The method according to claim 1, wherein R$^1$ is hydrogen, R$^2$ is NH$_2$, R$^3$ is cyano, R$^4$ is hydrogen or methyl, q is 0, and A is aryl which may be substituted or a aromatic heterocyclyl which may be substituted.

3. The method according to claim 1, wherein the said pyrrole derivative is selected from the group consisting of:

(1) 2-Amino-3-cyano-5-(2-fluorophenyl)-4-methylpyrrole;

(2) 2-Amino-3-cyano-4-methyl-5-phenylpyrrole;

(3) 2-Amino-5-(3-chlorophenyl)-3-cyano-4-methylpyrrole;

(4) 2-Amino-3-cyano-5-(2-furyl)-4-methylpyrrole;

(5) 2-Amino-3-cyano-5-(3,4-methylenedioxyphenyl) pyrrole;

(6) 2-Amino-3-cyano-5-(2,4-difluorophenyl)pyrrole;

(7) 5-(3-Chlorophenyl)-3-cyano-2-methylpyrrole;

(8) 2-Amino-3-cyano-4-methyl-5-(3-nitrophenyl)pyrrole;

(9) 3-Cyano-2,4-dimethyl-5-phenylpyrrole;

(10) 3-Cyano-5-(3-ethoxyphenyl)-2-pyrrolidinopyrrole; and

(11) 3-Cyano-5-(3,4-methylenedioxyphenyl)-2-pyrrolidino-pyrrole.

4. A method of treating hypertension in a subject comprising administering to the subject an effective amount of a pyrrole derivative of the formula [1] or pharmaceutically acceptable salt thereof;

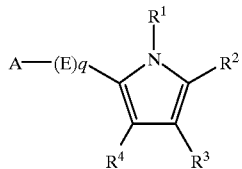

wherein R$^1$ represents hydrogen or alkoxycarbonylamino;

R$^2$ represents (i) alkyl, (ii) aryl which may be substituted, (iii) aromatic heterocyclyl which may be substituted, (iv) a group of the following formula [2]

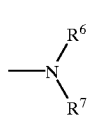

wherein R$^6$ and R$^7$ may be the same or different and each represents (1) hydrogen or (2) alkyl (said alkyl may be substituted by (1) aryl which may be substituted by alkoxy, or (2) aromatic heterocyclyl, or (3) hydroxy), or (v) a group of the following formula [3]

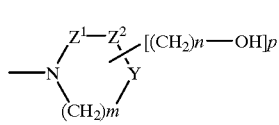

Z$^1$ and Z$^2$ may be the same or different and each represents —CH$_2$— or >C=O; provided that Z$^1$ and Z$^2$ do not concurrently represent >C=O;

Y represents —CH$_2$—, —O—, —S—, or >NR$^9$;

R$^9$ represents hydrogen, alkyl, acyl, aryl, or aromatic heterocyclyl;

m represents an integer of 1–3; n represents an integer of 0–2; p represents 0 or 1;

in case R$^2$ represents aryl which is substituted or aromatic heterocyclyl which is substituted, the particular aryl or aromatic heterocyclyl may be substituted by 1–3 same or different members selected from the group consisting of (1) halogen, (2) alkyl which may be substituted by halogen, (3) cyano, (4) nitro, (5) alkoxycarbonyl, (6) hydroxy, (7) alkoxy (said alkoxy may be substituted by (1) halogen, (2) aryl which may be substituted by alkoxy, or (3) alkoxy), (8) —NHSO$_2$R$^{82}$, and (9) —NR$^{83}$R$^{84}$; or two adjacent substituent groups may jointly represent —O—(CH$_2$)$_t$—O— (t represents 1 or 2);

R$^{82}$ represents (1) alkyl or (2) aryl which may be substituted by alkyl;

R$^{83}$ and R$^{84}$ may be the same or different and each represents (1) hydrogen, (2) alkyl, or (3) acyl; or R$^{83}$ and R$^{84}$ jointly and taken together with the adjacent N atom represent 5- through 7-membered cyclic amino;

R$^3$ represents cyano or carbamoyl;

R$^4$ represents hydrogen or alkyl;

E represents alkylene; q represents 0 or 1;

A represents (1) methyl, (2) aryl which may be substituted, or (3) aromatic heterocyclyl which may be substituted;

in case A represents aryl which is substituted or aromatic heterocyclyl which is substituted, the particular aryl or aromatic heterocyclyl may be substituted by 1–3 same or different members selected from the group consisting of (1) halogen, (2) alkyl which may be substituted by halogen, (3) cyano, (4) nitro, (5) alkoxycarbonyl, (6) hydroxy, (7) alkoxy (said alkoxy may be substituted by (1) halogen, (2) aryl which may be substituted by alkoxy, or (3) alkoxy), (8) —NHSO$_2$R$^{92}$, and (9) —NR$^{93}$R$^{94}$; or two adjacent substituent groups may jointly represent —O—(CH$_2$)$_u$—O— (u represents 1 or 2);

R$^{92}$ represents (1) alkyl or (2) aryl which may be substituted by alkyl;

R$^{93}$ and R$^{94}$ may be the same or different and each represents (1) hydrogen, (2) alkyl, or (3) acyl; or R$^{93}$ and R$^{94}$ jointly and taken together with the adjacent N atom represent 5- through 7-membered cyclic amino;

A—(E)q, R$^4$, and the double bond of the pyrrole ring may jointly, i.e.

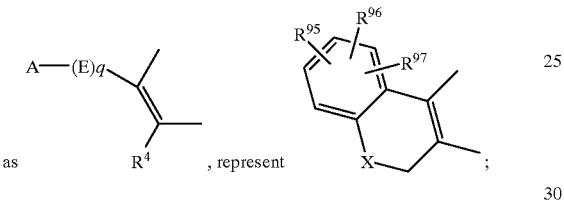

X represents —O—, —S—, or >NR$^{90}$ where R$^{90}$ represents alkyl; and

R$^{95}$, R$^{96}$ and R$^{97}$ may be the same or different and each is selected from the group consisting of (1) hydrogen, (2) halogen, (3) alkyl which may be substituted by halogen, (4) cyano, (5) nitro, (6) alkoxycarbonyl, (7) hydroxy, (8) alkoxy (said alkoxy may be substituted by halogen or alkoxy), (9) —NHSO$_2$R$^{92}$ (R$^{92}$ is as defined above), and (10) —NR$^{93}$R$^{94}$ (R$^{93}$ and R$^{94}$ are as defined above); any two adjacent substituent groups among R$^{95}$, R$^{96}$, and R$^{97}$ may jointly represent —O—(CH$_2$)$_u$—O— (u is as defined above).

5. The method according to claim 4, wherein R$^1$ is hydrogen, R$^2$ is NH$_2$, R$^3$ is cyano, R$^4$ is hydrogen or methyl, q is 0, and A is aryl which may be substituted or a aromatic heterocyclyl which may be substituted.

6. The method according to claim 4, wherein the said pyrrole derivative is selected from the group consisting of:

(1) 2-Amino-3-cyano-5-(2-fluorophenyl)-4-methylpyrrole;

(2) 2-Amino-3-cyano-4-methyl-5-phenylpyrrole;

(3) 2-Amino-5-(3-chlorophenyl)-3-cyano-4-methylpyrrole;

(4) 2-Amino-3-cyano-5-(2-furyl)-4-methylpyrrole;

(5) 2-Amino-3-cyano-5-(3,4-methylenedioxyphenyl)pyrrole;

(6) 2-Amino-3-cyano-5-(2,4-difluorophenyl)pyrrole;

(7) 5-(3-Chlorophenyl)-3-cyano-2-methylpyrrole;

(8) 2-Amino-3-cyano-4-methyl-5-(3-nitrophenyl)pyrrole;

(9) 3-Cyano-2,4-dimethyl-5-phenylpyrrole;

(10) 3-Cyano-5-(3-ethoxyphenyl)-2-pyrrolidinopyrrole; and

(11) 3-Cyano-5-(3,4-methylenedioxyphenyl)-2-pyrrolidino-pyrrole.

7. A method of treating asthma in a subject comprising administering to the subject an effective amount of a pyrrole derivative of the formula [1] or pharmaceutically acceptable salt thereof;

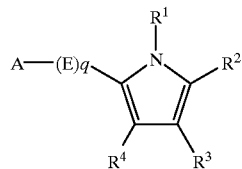

wherein R$^1$ represents hydrogen or alkoxycarbonylamino;

R$^2$ represents (i) alkyl, (ii) aryl which may be substituted, (iii) aromatic heterocyclyl which may be substituted, (iv) a group of the following formula [2]

wherein R$^6$ and R$^7$ may be the same or different and each represents (1) hydrogen or (2) alkyl (said alkyl may be substituted by (1) aryl which may be substituted by alkoxy, or (2) aromatic heterocyclyl, or (3) hydroxy), or (v) a group of the following formula [3]

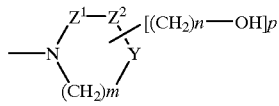

Z$^1$ and Z$^2$ may be the same or different and each represents —CH$_2$— or >C=O; provided that Z$^1$ and Z$^2$ do not concurrently represent >C=O;

Y represents —CH$_2$—, —O—, —S—, or >NR$^9$;

R$^9$ represents hydrogen, alkyl, acyl, aryl, or aromatic heterocyclyl;

m represents an integer of 1–3; n represents an integer of 0–2; p represents 0 or 1;

in case R$^2$ represents aryl which is substituted or aromatic heterocyclyl which is substituted, the particular aryl or aromatic heterocyclyl may be substituted by 1–3 same or different members selected from the group consisting of (1) halogen, (2) alkyl which may be substituted by halogen, (3) cyano, (4) nitro, (5) alkoxycarbonyl, (6) hydroxy, (7) alkoxy (said alkoxy may be substituted by (1) halogen, (2) aryl which may be substituted by alkoxy, or (3) alkoxy), (8) —NHSO$_2$R$^{82}$, and (9) —NR$^{83}$R$^{84}$; or two adjacent substituent groups may jointly represent —O—(CH$_2$)$_t$—O— (t represents 1 or 2);

R$^{82}$ represents (1) alkyl or (2) aryl which may be substituted by alkyl;

R$^{83}$ and R$^{84}$ may be the same or different and each represents (1) hydrogen, (2) alkyl, or (3) acyl; or R$^{83}$ and R$^{84}$ jointly and taken together with the adjacent N atom represent 5- through 7-membered cyclic amino;

$R^3$ represents cyano or carbamoyl;

$R^4$ represents hydrogen or alkyl;

E represents alkylene; q represents 0 or 1;

A represents (1) methyl, (2) aryl which may be substituted, or (3) aromatic heterocyclyl which may be substituted;

in case A represents aryl which is substituted or aromatic heterocyclyl which is substituted, the particular aryl or aromatic heterocyclyl may be substituted by 1–3 same or different members selected from the group consisting of (1) halogen, (2) alkyl which may be substituted by halogen, (3) cyano, (4) nitro, (5) alkoxycarbonyl, (6) hydroxy, (7) alkoxy (said alkoxy may be substituted by (1) halogen, (2) aryl which may be substituted by alkoxy, or (3) alkoxy), (8) —NHSO$_2$R$^{92}$, and (9) —NR$^{93}$R$^{94}$; or two adjacent substituent groups may jointly represent —O—(CH$_2$)$_u$—O— (u represents 1 or 2);

$R^{92}$ represents (1) alkyl or (2) aryl which may be substituted by alkyl;

$R^{93}$ and $R^{94}$ may be the same or different and each represents (1) hydrogen, (2) alkyl, or (3) acyl; or $R^{93}$ and $R^{94}$ jointly and taken together with the adjacent N atom represent 5- through 7-membered cyclic amino;

A—(E)q, R$^4$, and the double bond of the pyrrole ring may jointly, i.e.

as $$\text{A—(E)}q\diagdown\diagup\diagdown_{R^4} \quad , \text{represent} \quad \diagup^{R^{95}}\diagdown^{R^{96}}\diagup^{R^{97}}\diagdown_{X}\diagup ;$$

X represents —O—, —S—, or >NR$^{90}$ where R$^{90}$ represents alkyl; and $R^{95}$, $R^{96}$ and $R^{97}$ may be the same or different and each is selected from the group consisting of (1) hydrogen, (2) halogen, (3) alkyl which may be substituted by halogen, (4) cyano, (5) nitro, (6) alkoxycarbonyl, (7) hydroxy, (8) alkoxy (said alkoxy may be substituted by halogen or alkoxy), (9) —NHSO$_2$R$^{92}$ (R$^{92}$ is as defined above), and (10) —NR$^{93}$R$^{94}$ (R$^{93}$ and R$^{94}$ are as defined above); any two adjacent substituent groups among R$^{95}$, R$^{96}$, and R$^{97}$ may jointly represent —O—(CH$_2$)$_u$—O— (u is as defined above).

8. The method according to claim 7, wherein R$^1$ is hydrogen, R$^2$ is NH$_2$, R$^3$ is cyano, R$^4$ is hydrogen or methyl, q is 0, and A is aryl which may be substituted or a aromatic heterocyclyl which may be substituted.

9. The method according to claim 7, wherein the said pyrrole derivative is selected from the group consisting of:

(1) 2-Amino-3-cyano-5-(2-fluorophenyl)-4-methylpyrrole;

(2) 2-Amino-3-cyano-4-methyl-5-phenylpyrrole;

(3) 2-Amino-5-(3-chlorophenyl)-3-cyano-4-methylpyrrole;

(4) 2-Amino-3-cyano-5-(2-furyl)-4-methylpyrrole;

(5) 2-Amino-3-cyano-5-(3,4-methylenedioxyphenyl) pyrrole;

(6) 2-Amino-3-cyano-5-(2,4-difluorophenyl)pyrrole;

(7) 5-(3-Chlorophenyl)-3-cyano-2-methylpyrrole;

(8) 2-Amino-3-cyano-4-methyl-5-(3-nitrophenyl)pyrrole;

(9) 3-Cyano-2,4-dimethyl-5-phenylpyrrole;

(10) 3-Cyano-5-(3-ethoxyphenyl)-2-pyrrolidinopyrrole; and

(11) 3-Cyano-5 (3,4-methylenedioxyphenyl)-2-pyrrolidino-pyrrole.

10. A method of treating trichogenetic insufficiency, psilosis or alopecia in a subject comprising administering to the subject an effective amount of a pyrrole derivative of the formula [1] or pharmaceutically acceptable salt thereof;

[1]

$$A—(E)q\diagdown\diagup_{R^4}\diagdown^{R^1}\diagup^{N}\diagdown_{R^3}\diagup^{R^2}$$

wherein R$^1$ represents hydrogen or alkoxycarbonylamino;

R$^2$ represents (i) alkyl, (ii) aryl which may be substituted, (iii) aromatic heterocyclyl which may be substituted, (iv) a group of the following formula [2]

[2]

$$—N\diagdown^{R^6}_{R^7}$$

wherein R$^6$ and R$^7$ may be the same or different and each represents (1) hydrogen or (2) alkyl (said alkyl may be substituted by (1) aryl which may be substituted by alkoxy, or (2) aromatic heterocyclyl, or (3) hydroxy), or (v) a group of the following formula [3]

[3]

$$—N\diagup^{Z^1-Z^2}\diagdown_{Y}\diagup^{[(CH_2)n—OH]p}$$
$$\diagdown_{(CH_2)m}\diagup$$

$Z^1$ and $Z^2$ may be the same or different and each represents —CH$_2$— or >C=O; provided that $Z^1$ and $Z^2$ do not concurrently represent >C=O;

Y represents —CH$_2$—, —O—, —S—, or >NR$^9$;

R$^9$ represents hydrogen, alkyl, acyl, aryl, or aromatic heterocyclyl;

m represents an integer of 1–3; n represents an integer of 0–2; p represents 0 or 1;

in case R$^2$ represents aryl which is substituted or aromatic heterocyclyl which is substituted, the particular aryl or aromatic heterocyclyl may be substituted by 1–3 same or different members selected from the group consisting of (1) halogen, (2) alkyl which may be substituted by halogen, (3) cyano, (4) nitro, (5) alkoxycarbonyl, (6) hydroxy, (7) alkoxy (said alkoxy may be substituted by (1) halogen, (2) aryl which may be substituted by alkoxy, or (3) alkoxy), (8) —NHSO$_2$R$^{82}$, and (9) —NR$^{83}$R$^{84}$; or two adjacent substituent groups may jointly represent —O—(CH$_2$)$_t$—O— (t represents 1 or 2);

$R^{82}$ represents (1) alkyl or (2) aryl which may be substituted by alkyl;

$R^{83}$ and $R^{84}$ may be the same or different and each represents (1) hydrogen, (2) alkyl, or (3) acyl; or $R^{83}$ and $R^{84}$ jointly and taken together with the adjacent N atom represent 5- through 7-membered cyclic amino;

$R^3$ represents cyano or carbamoyl;

$R^4$ represents hydrogen or alkyl;

E represents alkylene; q represents 0 or 1;

A represents (1) methyl, (2) aryl which may be substituted, or (3) aromatic heterocyclyl which may be substituted;

in case A represents aryl which is substituted or aromatic heterocyclyl which is substituted, the particular aryl or aromatic heterocyclyl may be substituted by 1–3 same or different members selected from the group consisting of (1) halogen, (2) alkyl which may be substituted by halogen, (3) cyano, (4) nitro, (5) alkoxycarbonyl, (6) hydroxy, (7) alkoxy (said alkoxy may be substituted by (1) halogen, (2) aryl which may be substituted by alkoxy, or (3) alkoxy), (8) —NHSO$_2$R$^{92}$, and (9) —NR$^{93}$R$^{94}$; or two adjacent substituent groups may jointly represent —O—(CH$_2$)$_u$—O— (u represents 1 or 2);

$R^{92}$ represents (1) alkyl or (2) aryl which may be substituted by alkyl;

$R^{93}$ and $R^{94}$ may be the same or different and each represents (1) hydrogen, (2) alkyl, or (3) acyl; or $R^{93}$ and $R^{94}$ jointly and taken together with the adjacent N atom represent 5- through 7-membered cyclic amino;

A—(E)q, $R^4$, and the double bond of the pyrrole ring may jointly, i.e.

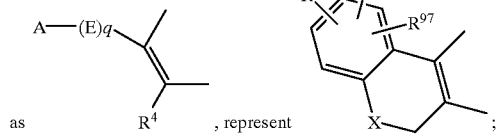

as , represent ;

X represents —O—, —S—, or >NR$^{90}$ where $R^{90}$ represents alkyl; and $R^{95}$, $R^{96}$ and $R^{97}$ may be the same or different and each is selected from the group consisting of (1) hydrogen, (2) halogen, (3) alkyl which may be substituted by halogen, (4) cyano, (5) nitro, (6) alkoxycarbonyl, (7) hydroxy, (8) alkoxy (said alkoxy may be substituted by halogen or alkoxy), (9) —NHSO$_2$R$^{92}$ (R$^{92}$ is as defined above), and (10) —NR$^{93}$R$^{94}$ (R$^{93}$ and R$^{94}$ are as defined above); any two adjacent substituent groups among $R^{95}$, $R^{96}$, and $R^{97}$ may jointly represent —O—(CH$_2$)$_u$—O— (u is as defined above).

11. The method according to claim 10, wherein $R^1$ is hydrogen, $R^2$ is NH$_2$, $R^3$ is cyano, $R^4$ is hydrogen or methyl, q is 0, and A is aryl which may be substituted or a aromatic heterocyclyl which may be substituted.

12. The method according to claim 10, wherein the said pyrrole derivative is selected from the group consisting of:

(1) 2-Amino-3-cyano-5-(2-fluorophenyl)-4-methylpyrrole;

(2) 2-Amino-3-cyano-4-methyl-5-phenylpyrrole;

(3) 2-Amino-5-(3-chlorophenyl)-3-cyano-4-methylpyrrole;

(4) 2-Amino-3-cyano-5-(2-furyl)-4-methylpyrrole;

(5) 2-Amino-3-cyano-5-(3,4-methylenedioxyphenyl)pyrrole;

(6) 2-Amino-3-cyano-5-(2,4-difluorophenyl)pyrrole;

(7) 5-(3-Chlorophenyl)-3-cyano-2-methylpyrrole;

(8) 2-Amino-3-cyano-4-methyl-5-(3-nitrophenyl)pyrrole;

(9) 3-Cyano-2,4-dimethyl-5-phenylpyrrole;

(10) 3-Cyano-5-(3-ethoxyphenyl)-2-pyrrolidinopyrrole; and

(11) 3-Cyano-5-(3,4-methylenedioxyphenyl)-2-pyrrolidino-pyrrole.

* * * * *